United States Patent

Kume et al.

[11] Patent Number: 4,692,436
[45] Date of Patent: Sep. 8, 1987

[54] PHOSPHOROIMIDATES AS PESTICIDES

[75] Inventors: Toyohiko Kume; Shinichi Tsuboi; Kunihiro Isono, all of Hino, Japan

[73] Assignee: Nihon Tokushu Noyaku Seizo K.K., Tokyo, Japan

[21] Appl. No.: 861,471

[22] Filed: May 9, 1986

[30] Foreign Application Priority Data

May 14, 1985 [JP] Japan .................... 60-100607

[51] Int. Cl.$^4$ .................... A01N 57/02; C07F 9/24
[52] U.S. Cl. .................... 514/129; 558/185
[58] Field of Search .................... 558/185; 514/129

[56] References Cited

U.S. PATENT DOCUMENTS 3,903,207 9/1975 Hoffmann et al. .................... 558/185

FOREIGN PATENT DOCUMENTS 2260576 6/1973 Fed. Rep. of Germany .
1373893 11/1974 United Kingdom .

*Primary Examiner*—Anton H. Sutto
*Attorney, Agent, or Firm*—Sprung Horn Kramer & Woods

[57] ABSTRACT

Novel phosphoroimidates of the formula

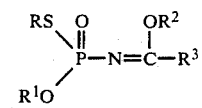

wherein
R represents n-propyl or sec.-butyl,
$R^1$ represents methyl or ethyl,
$R^2$ represents methyl or ethyl, and
$R^3$ represents alkyl having from 3 to 4 carbon atoms, and the use of the new compounds as insecticides, acaricides and nematicides.

10 Claims, No Drawings

PHOSPHOROIMIDATES AS PESTICIDES

The present invention relates to novel phosphoroimidates, to a process for their preparation and to their use as insecticides, acaricides and nematicides.

It has already been disclosed that certain phosphoroimidates have insecticidal and acaricidal activities (see Japanese laid-open Pat. No. 67437/1973 or DE-A-2,260,576).

There have now been found novel phosphoroimidates of the formula (I)

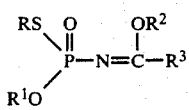   (I)

wherein
R represents n-propyl or sec-butyl (preferably n-propyl),
$R^1$ represents methyl or ethyl (preferably ethyl),
$R^2$ represents methyl or ethyl (preferably ethyl), and
$R^3$ represents alkyl having 3 to 4 carbon atoms (preferably n- or i-propyl or n-butyl).

The compounds of the formula (I) are obtained when
(a) compounds of the formula (II)

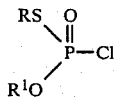   (II)

wherein R and $R^1$ have the same meanings as above, are reacted with compounds of the formula (III)

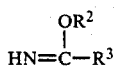   (III)

wherein $R^2$ and $R^3$ have the same meanings as above, in the presence of inert solvents, if appropriate in the presence of acid acceptors, or
(b) compounds of the formula (IV)

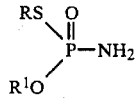   (IV)

wherein R and $R^1$ have the same meanings as above, are reacted with compounds of the formula (V)

$R^3$—C(OR$^2$)$_3$   (V)

wherein $R^2$ and $R^3$ have the same meanings as above, in the presence of inert solvents.

The novel phosphoroimidates exhibit powerful insecticidal, acaricidal and nematicidal properties.

Surprisingly, the phosphoroimidates according to the invention exhibit a substantially greater insecticidal, acaricidal and nematicidal action than those known from the aforesaid prior art.

In the general formulae alkyl $R^3$ means straight-chain or branched propyl or butyl, i.e. n- and i-propyl or n-, i-, sec- and tert-butyl, preferably n- and i-propyl or n-$C_4H_9$, particularly preferably n- and i-propyl.

Among the phosphoroimidates according to the invention, of the formula (I), preferred compounds are those
in which
R represents n-propyl or sec-butyl,
$R^1$ represents ethyl,
$R^2$ represents ethyl, and
$R^3$ represents n- or i-propyl or n-, i- or sec-butyl.

Particularly preferred phosphoroimidates of the formula (I) are those
in which
R represents n-propyl,
$R^1$ represents ethyl,
$R^2$ represents ethyl, and
$R^3$ represents n- or i-propyl.

Specifically, the following compounds may be mentioned:
Ethyl N-(O-ethyl S-n-propylthiophosphoryl)isobutyroimidate,
Ethyl N-(O-ethyl S-n-propylthiophosphoryl)butyroimidate.

If, for example, in process (a), O-ethyl S-n-propyl phosphorochloridothioate and ethyl isobutyroimidate are used as starting materials, the course of the reaction can be represented by the following equation:

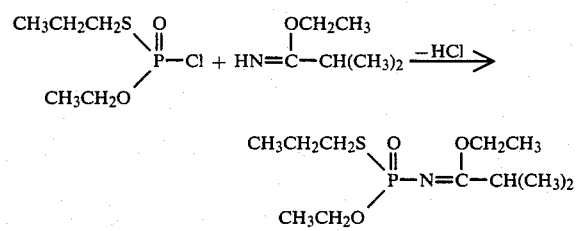

If, for example, in process (b), O-ethyl S-n-propyl phoshorothioamidate and 1,1,1-triethoxybutane are used as starting materials, the course of the reaction can be represented by the following equation:

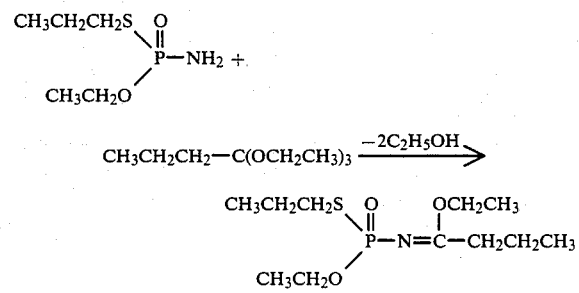

The compounds of the formula (II) usable according to the invention are already known in the field of organic phosphorus chemistry.

As examples, there may be mentioned:
O-ethyl S-n-propyl phosphorochloridothioate and
O-ethyl S-sec-butyl phosphorochloridothioate.

The compounds of the formula (III) usable according to the invention are, for the most part, are already known in the field of organic chemistry.

As examples, there may be mentioned:
Ethyl isobutyroimidate,
Ethyl butyroimidate,
Ethyl valeroimidate,
Ethyl isovaleroimidate, and
Ethyl pivaloimidate.

The compounds of the formula (III) can easily be synthesized, for example, by the method described in Bull. Soc. Chim, France, 1964, No. 11, pp 2997–2999.

Suitable diluents in process (a) are all inert solvents. These preferably include aliphatic, cycloaliphatic and aromatic hydrocarbons (which may optionally be chlorinated), for example, hexane, cyclohexane, petroleum ether, ligroin, benzene, toluene, xylene, methylene chloride, chloroform, carbon tetrachloride, ethylene chloride, trichloroethylene and chlorobenzene; ethers, for example, diethyl ether, methyl ethyl ether, di-isopropyl ether, dibutyl ether, dioxane and tetrahydrofuran; ketones, for example, acetone, methyl ethyl ketone, methyl-isopropyl ketone and methyl-isobutyl ketone; nitriles, for example, acetonitrile, propionitrile and acrylonitrile; esters, for example, ethyl acetate and amyl acetate; acid amides, for example, dimethyl formamide and dimethyl acetoamide; sulfone and sulfoxides, for example, dimethyl sulfoxide and sulfolan and bases such as pyridine.

Further, the above-process (a) can be carried out in the presence of acid acceptors. The acid binders can include the hydroxides, carbonates or hydrogen carbonates of potassium or sodium employed ordinarily, as well as tertiary amines, for example, triethylamine, diethylaniline and pyridine.

The reaction temperatures can be varied within a substantial range.

In general, the reaction is carried out at between about −20° C. and about 100° C., preferably between about 0° C. and about 60° C.

The reaction can be carried out under normal pressure and also under elevated pressure. In general, it is carried out under ambient pressure.

In carrying out the process (a), the compounds of the formula (I) can be synthesized by reacting the compounds of the formula (III) in about 1–3 molar amounts and, preferably, about 1.5–2.5 amounts per mol of the compounds of the formula (II) in the presence of inert solvents.

In the above process (b), the starting materials of the formula (IV) and (V) are compounds which have been already well known in the organic chemistry or which can be prepared according to known methods.

The process (b) can be carried out according to known methods (see, for example, Japanese Patent Laid-Open No. 67437-1973 or DE-A-2,260,576).

Preferably the compounds of formula (IV) are reacted with the compounds of formula (V) in the presence of a solution of hydrochloric acid in an alcohol (as methanol, ethanol or propanol) and optionally in the presence of inert organic solvents as they are described for process (a) above, preferably in the presence of acetonitrile.

The reaction is generally carried out at temperatures between 10° and 120° C., preferably between 60° and 100° C., under normal or elevated pressure. In carrying out process (b) one mol of the compounds of the formula (IV) is reacted with 0.8 to 2.5, preferably with 1.0 to 1.5 mols, of the compounds of formula (V). The end products of formula (I) are isolated according to known methods, e.g. by distilling off the solvents under vacuum.

The active substances according to the invention exhibit powerful insecticidal, acaricidal and nematicidal effects, in particular remarkable effects against soil insects.

They can therefore be applied for controlling various harmful insects.

The active substances have also systemic action. In particular, examples of harmful insects against which they are active include the following: Coleopterous, for example, *Callosobruchus chinensis, Sitophilus zeamais, Tribolium castaneum, Epilachna vigitioctomaculata, Agriotes fuscicollis, Anomala refucuprea, Leptinotarsa decemlineata,* Diabrotica spp., *Monochamus alternatus, Lissorhoptrus oryzophilus* and *Lyctus brunneus;*

Lepidoptera, for example, *Lymantria dispar, Malacosoma neustria, Pieris rapae, Spodoptera litura, Mamestra brassicae, Chilo suppressalis, Pyrausta nubilalis, Ephestia cautella, Adoxophyes orana, Carpocapsa pomonella, Agrotis fucosa, Galleria mellonella, Plutella maculipennis* and *Phyllocnistis citrella;*

Hemiptera, for example, *Nephotettix cincticeps, Nilaparvata lugens, Psuodococcus comstocki, Unaspis yanonensis, Myzus persicae, Aphis pomi, Aphis gossypii, Rhopalosiphum pseudobrassicas, Stephanitis nashi,* Nazara spp., *Cimex lectularius, Trialeurodes vaporariorum* and Psylla spp.;

Orthoptera, for example, *Blatella germanica, Periplaneta americana, Gryllotalpa africana, Locusta migratoria migratoriodes;*

Isoptera, for example, *Deucotermes speratus* and *Coptotermes formosanus;*

Diptera, for example, *Musca domestica, Aedes aegypti, Hylemia platura, Culex pipiens, Anopheles slnensis* and *Culex tritaeniorhynchus.*

Mites can include, for example, *Tetranychus telarius, Tetranychus ulticae, Panonychus citri, Aculus pelekassi* and Tnrronomus spp.

Nematodes can include, for example, *Meloidogyne incognita, Bursaphelenchus lignicolus Mamiya et Kiyohara, Aphelenchoides besseyi, Heterodera glycines* and Pratylenchus spp.

Furthermore in the fields of animal farming and husbandry, the novel compounds according to this invention can effectively be used against various deleterious animal parasites, for example, ticks, insects and nematodes. Examples of such animal parasites include the following:

Ticks, as for example, Oranithodoros spp., Ixodes spp., Boophilus spp.

Insects, as for example, Gastophilus spp., Stomoxys spp., Trichlodectes spp., Rhodnius spp. and *Ctenocephalides canis.*

The active compounds can be converted into the customary formulations, such as solutions, emulsions, suspensions, powders, foams, pastes, granules, aerosols, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethyl-sulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulation.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas, substances produced by microorganisms.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 100% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

The following examples illustrate the present invention more specifically. The invention is however not to be limited thereto.

EXAMPLE 1

(Compound No. 1)

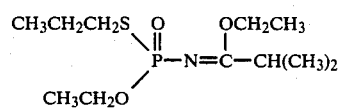

O-ethyl S-n-propyl phosphochloridothioate (8.10 g) is dissolved in toluene (40 ml) and ethyl isobutyroimidate (10.12 g) was added dropwise to the solution at 0° C. After stirring at room temperature for 16 hours and, further, at 60° C. for 4 hours, the toluene solution was washed with water, 2% hydrochloric acid and 5% aqueous solution of potassium hydroxide and water successively and then dried over anhydrous sodium sulfate. By distilling off solvent under reduced pressure, 9.61 g of crude oily product were obtained. The crude product was purified by distillation under reduced pressure to obtain ethyl N-(O-ethyl-S-n-propylthiophosphoryl)isobutyroimidate (5.73 g). $n_D^{20}$ 1.4745

Compounds according to this invention obtainable by the same method as in Example 1 are shown in Table 1 below.

TABLE 1

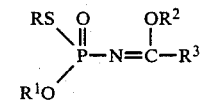

| Compound No. | R | $R^1$ | $R^2$ | $R^3$ | |
|---|---|---|---|---|---|
| 2 | n-$C_3H_7$ | —$C_2H_5$ | —$C_2H_5$ | n-$C_3H_7$ | $n_D^{20}$ 1.4766 |
| 3 | sec-$C_4H_9$ | —$C_2H_5$ | —$C_2H_5$ | n-$C_3H_7$ | $n_D^{20}$ 1.4762 |
| 4 | n-$C_3H_7$ | —$C_2H_5$ | —$CH_3$ | iso-$C_3H_7$ | $n_D^{20}$ 1.4252 |
| 5 | sec-$C_4H_9$ | —$C_2H_5$ | —$CH_3$ | iso-$C_3H_7$ | $n_D^{20}$ 1.4230 |
| 6 | sec-$C_4H_9$ | —$C_2H_5$ | —$C_2H_5$ | iso-$C_3H_7$ | $n_D^{20}$ 1.4740 |
| 7 | n-$C_3H_7$ | —$C_2H_5$ | —$C_2H_5$ | n-$C_4H_9$ | $n_D^{20}$ 1.4752 |
| 8 | sec-$C_4H_9$ | —$C_2H_5$ | —$C_2H_5$ | n-$C_4H_9$ | $n_D^{20}$ 1.4745 |
| 9 | n-$C_3H_7$ | —$C_2H_5$ | —$C_2H_5$ | sec-$C_4H_9$ | |
| 10 | sec-$C_4H_9$ | —$C_2H_5$ | —$C_2H_5$ | sec-$C_4H_9$ | |
| 11 | n-$C_3H_7$ | —$C_2H_5$ | —$C_2H_5$ | iso-$C_4H_9$ | |
| 12 | sec-$C_4H_9$ | —$C_2H_5$ | —$C_2H_5$ | iso-$C_4H_9$ | |
| 13 | n-$C_3H_7$ | —$C_2H_5$ | —$C_2H_5$ | tert-$C_4H_9$ | |

USE EXAMPLE

Comparison

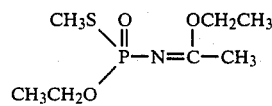

A-1

-continued

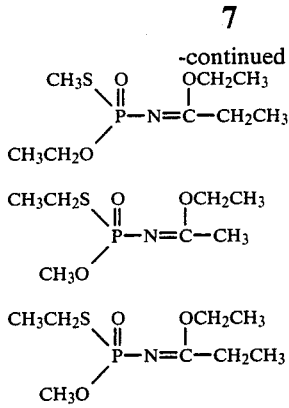

A-1, A-2, A-3 and A-4 are compounds described in Japanese Patent Laid-Open No. 67437/1973 or DE-A-2,260,576.

EXAMPLE 2

Test against *Nephotettix cincticeps* resistant to organic phosphorus agents
Preparation of tested chemical solution
Solvent: Xylol; 3 parts by weight
Emulsifier: Polyoxyethylene alkylphenyl ether; 1 part by weight
For preparing a formulation of an appropriate active compound, one part by weight of the active compound was mixed with the solvent in the above-specified amount containing the emulsifier in the above-specified amount, and then the mixture was diluted with water to a predetermined concentration.
Test Method:
A solution of the active compound prepared and diluted with water to a predetermined concentration as above was sprayed onto *Oryza sativa* of about 10 cm height planted in a pot of 12 cm diameter, 10 ml per pot. After drying the sprayed chemical solution, each pot was covered with a metal cage 7 cm in diameter and 14 cm in height, and 30 adult female *Nephotettix cincticeps* showing resistance to organic phosphorus agents were released into the cage. After keeping them in a thermostatic chamber, the number of dead insects after 2 days was counted to calculate the insecticidal rate.
Typical results are in Table 2.

TABLE 2

| | Insecticidal rate (%) Active ingredient concentration (ppm) | | | | |
|---|---|---|---|---|---|
| | 1000 | 200 | 40 | 8 | 1.6 |
| Compound No. | | | | | |
| 1 | 100 | 100 | 100 | 100 | 100 |
| 2 | 100 | 100 | 100 | 100 | |
| 3 | 100 | 100 | 100 | | |
| 4 | 100 | 100 | 100 | | |
| Comparison | | | | | |
| A-1 | 100 | 60 | 0 | | |
| A-2 | 90 | 0 | | | |
| A-3 | 100 | 0 | | | |
| A-4 | 100 | 20 | 0 | | |

EXAMPLE 3

Test against *Tetranychus telarius* (Spray treatment)
Test Method:
Leaves of 2-foliage leaf stage of *Phaseolus vulgaris* cultivated in a pot of 6 cm in diameter, were inoculated with 50-100 adult *Tetranychus telarius* resistant to organic phosphorus agents. Two days after the inoculation, 40 ml per pot of a solution of the active compound, prepared in the same manner and diluted with water to a preterminated concentration as in Example 2, was sprayed on each plant, the plant was kept in a greenhouse, and the controlling effect was evaluated 10 days layer, the controlling effect is defined as follows:
3: Survived adult; 0%
2: Survived adult; 0-5% of the not-treated case
1: Survived adult; 5-50% of the not-treated case
0: Survived adult; more than 50% of the not-treated case
Typical results are shown in Table 3.

TABLE 3

| | Insecticidal rate (%) Active ingredient concentration (ppm) | | | |
|---|---|---|---|---|
| | 1000 | 200 | 40 | 8 |
| Compound No. | | | | |
| 1 | 3 | 3 | 3 | |
| 2 | 3 | 3 | 3 | 3 |
| 3 | 3 | 3 | 3 | |
| Comparison | | | | |
| A-1 | 0 | | | |
| A-2 | 0 | | | |
| A-3 | 0 | | | |
| A-4 | 1 | 0 | | |

EXAMPLE 4

Test against *Tetranychus telarius* (Systemic activity test)
Test Method:
Leaves of 2-dicotyledonous stage of *Phaseolus vulgaris* cultivated in a pot of 9 cm diameter, were inoculated with 50-100 adult *Tetranychus telarius*. Two days after the inoculation, 20 ml of a solution of the active compound prepared and diluted with water to a predetermined concentration in the same manner as in Example 2 was watered near the root and the plants were then stored in a greenhouse. The controlling effect was evaluated 10 days later. The controlling effect is defined as follows:
3: Survived adult; 0%
2: Survived adult; 0-5% of the not-treated case
1: Survived adult; 5-50% of the not-treated case
0: Survived adult; more than 50% of the not-treated case
Typical results are shown in Table 4.

TABLE 4

| | Insecticidal rate (%) Active ingredient concentration (ppm) | | | |
|---|---|---|---|---|
| | 1000 | 200 | 40 | 8 |
| Compound No. | | | | |
| 1 | 3 | 3 | 3 | 3 |
| 2 | 3 | 3 | 3 | 3 |
| 3 | 3 | 3 | 3 | |
| Comparison | | | | |
| A-1 | 1 | 0 | | |
| A-2 | 0 | | | |
| A-3 | 0 | | | |
| A-4 | 0 | | | |

EXAMPLE 5

Test against *Meloidogyne incognita*

Preparation of tested chemical solution
2 parts of an active compound and 98 parts of talc were pulverized and mixed.
Test Method:

The active compound prepared as above was applied to soils contaminated with *Meloidogyne incognita in a chemical dose of* 50, 25, 10, 5 and 2.5 ppm, uniformly mixed under stirring and then filled in pots each of 1/5000 are. Seeds of tomato (variety: Kurihara) were sown by about 20 seeds per pot, the pots placed in a greenhouse and, four weeks later, roots thereof were dug out carefully so as not to injure them. The degree of damage for 10 roots among them was classified and evaluated based on the following standards to determine the root knot index.

Degree of damage
0: No knot formed (complete control)
1: Knot formed slightly
3: Knot formed remarkably
4: Knot formed most remarkably (corresponding to not-treated case)

Root knot index =

$$\frac{\Sigma \text{ (class value} \times \text{ individual number)}}{\text{Total individual number investigated} \times 4} \times 100$$

The evaluation was made by the controlling effect in accordance with the following equation:

Controlling effect =

$$\frac{\text{root knot index in the not-treated lot} - \text{root knot index in the treated lot}}{\text{root knot index not treated lot}} \times 100$$

100% controlling effect means complete control. Typical results are shown in Table 5.

TABLE 5

| | Insecticidal rate (%) Active ingredient concentration (ppm) | | | | |
|---|---|---|---|---|---|
| | 50 | 25 | 10 | 5 | 2.5 |
| Compound No. | | | | | |
| 1 | 100 | 100 | 100 | 100 | 89 |
| 2 | 100 | 100 | 100 | 98 | 70 |
| 3 | 100 | 100 | 100 | 100 | 82 |
| 4 | 100 | 100 | 100 | 100 | 100 |
| Comparison | | | | | |
| A-1 | 0 | | | | |
| A-2 | 0 | | | | |
| A-3 | 0 | | | | |
| A-4 | 0 | | | | |

EXAMPLE 6

Test against *Hylemia platura*

Test Method:

The active compound prepared in the same manner as in Example 5 was applied at the chemical dose of 50, 25, 10 and 5 ppm to each of the tested soils and uniformly stirred and mixed, and the soils were filled into 1/5000 are pots. Then, seeds of *Allium cepa* (variety: Hayate) were sown, about 100 seeds per pot, and the plants cultivated in a greenhouse. Two weeks later, about 200 of 1st instar larvae of *Hylemia platura* were inoculated per pot and, two weeks after the inoculation, seedlings of *Allium cepa* were dug out. The degree of damage was classified and evaluated based on the following standards to determine the controlling effect.

Degree of damage:
0: no damage
1: slight damage
2: moderate damage
3: intense damage
4: death Damage index =

$$\frac{\Sigma \text{ (degree of damage)} \times \text{ (individual number)}}{\text{Total number investigated} \times 4} \times 100$$

Controlling effect =

$$\frac{\left(\begin{array}{c}\text{damage index in}\\\text{the not-treated lot}\end{array}\right) - \left(\begin{array}{c}\text{damage index in}\\\text{the treated lot}\end{array}\right)}{\text{damage index not-treated lot}} \times 100$$

Typical results are shown in Table 6.

TABLE 6

| | Controlling effect Active ingredient concentration (ppm) | | | |
|---|---|---|---|---|
| | 50 | 25 | 10 | 5 |
| Compound No. | | | | |
| 1 | 100 | 100 | 100 | 100 |
| 2 | 100 | 100 | 100 | 100 |
| 3 | 100 | 100 | 100 | 100 |
| Comparison | | | | |
| A-1 | 80 | 0 | | |
| A-4 | 40 | 0 | | |

It will be understood that the specification and examples are illustrative but not limitative of the present invention and that other embodiments within the spirit and scope of the invention will suggest themselves to those skilled in the art.

What is claimed:

1. A phosphoroimidate of the formula

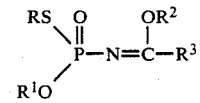

wherein
R represents n-propyl or sec.-butyl,
$R^1$ represents methyl or ethyl,
$R^2$ represents methyl or ethyl, and
$R^3$ represents alkyl having from 3 to 4 carbon atoms.

2. A compound according to claim 1, wherein
R is n-propyl or sec.-butyl,
$R^1$ is ethyl,
$R^2$ is ethyl, and
$R^3$ is n-propyl, i-propyl, n-butyl, i-butyl or sec.-butyl.

3. A compound according to claim 1, wherein
R is n-propyl,
$R^1$ is ethyl,
$R^2$ is ethyl, and
$R^3$ is n-propyl or i-propyl.

4. A compound according to claim 1, wherein such compound is ethyl N-(O-ethyl-S-n-propylthiophosphoryl)isobutyroimidate of the formula

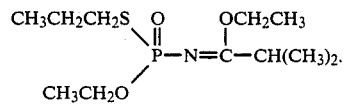

5. A compound according to claim 1, wherein such compound is ethyl N-(O-ethyl S-n-propylthiophosphoryl)butyroimidate of the formula

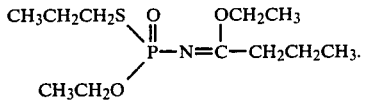

6. A compound according to claim 1, wherein such compound is ethyl N-(O-ethyl S-sec.-butylthiophosphoryl)butyroimidate of the formula

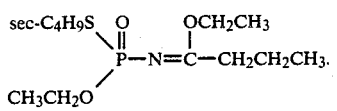

7. A compound according to claim 1, wherein such compound is methyl N-(O-ethyl-S-n-propylthiophosphoryl)isobutyroimidate of the formula

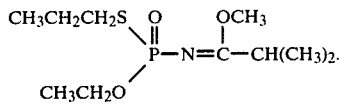

8. An insecticidal, acaricidal or nematicidal composition comprising an insecticidally, acaricidally or nematicidally effective amount of a compound according to claim 1 in admixture with a diluent.

9. A method of combating insects, acarids or nematodes which comprises applying thereto or to a habitat thereof an insecticidally, acaricidally or nematicidally effective amount of a compound according to claim 1.

10. The method according to claim 9, wherein such compound is
ethyl N-(O-ethyl S-n-propylthiophosphoryl)isobutyroimidate,
ethyl N-(O-ethyl S-n-propylthiophosphoryl)butyroimidate,
ethyl N-(O-ethyl S-sec.-butylthiophosphoryl)butyroimidate or
methyl N-(O-ethyl-S-n-propylthiophosphoryl)isobutyroimidate.

* * * * *